United States Patent [19]
Johnson et al.

[11] Patent Number: 6,098,629
[45] Date of Patent: Aug. 8, 2000

[54] SUBMUCOSAL ESOPHAGEAL BULKING DEVICE

[75] Inventors: George Johnson, Santa Ana; Ross Tsukashima, San Diego, both of Calif.

[73] Assignee: Endonetics, Inc., San Diego, Calif.

[21] Appl. No.: 09/287,607

[22] Filed: Apr. 7, 1999

[51] Int. Cl.⁷ ................................................. A61B 19/00
[52] U.S. Cl. ............................................................. 128/897
[58] Field of Search ................................ 128/897; 623/11

[56] References Cited

U.S. PATENT DOCUMENTS

| | | |
|---|---|---|
| 4,183,102 | 1/1980 | Guiset . |
| 4,439,872 | 4/1984 | Henley-Cohn et al. . |
| 4,636,213 | 1/1987 | Pakiam . |
| 4,740,208 | 4/1988 | Cavon . |
| 4,820,303 | 4/1989 | Brauman . |
| 4,955,907 | 9/1990 | Ledergerber . |
| 4,963,150 | 10/1990 | Brauman . |
| 5,002,583 | 3/1991 | Pitaru et al. . |
| 5,336,263 | 8/1994 | Ersek et al. . |
| 5,554,185 | 9/1996 | Block et al. . |
| 5,658,330 | 8/1997 | Carlisle et al. . |
| 5,667,778 | 9/1997 | Atala . |
| 5,779,734 | 7/1998 | Ledergerber . |

FOREIGN PATENT DOCUMENTS

| | | |
|---|---|---|
| 0 628 292 A1 | 12/1994 | European Pat. Off. . |
| 1655469 A1 | 6/1991 | U.S.S.R. . |

*Primary Examiner*—Max Hindenburg
*Assistant Examiner*—Brian Szmal
*Attorney, Agent, or Firm*—Knobbe, Martens, Olson & Bear, LLP

[57] ABSTRACT

Disclosed is a prosthetic bulking device for implantation below the mucosa to treat gastroesophageal reflux disease. The bulking device comprises a flexible body which may have one or more attachment surfaces to allow tissue ingrowth from the adjacent tissue. The bulking device cooperates with residual lower esophageal sphincter (LES) function to increase LES closing pressure.

24 Claims, 7 Drawing Sheets

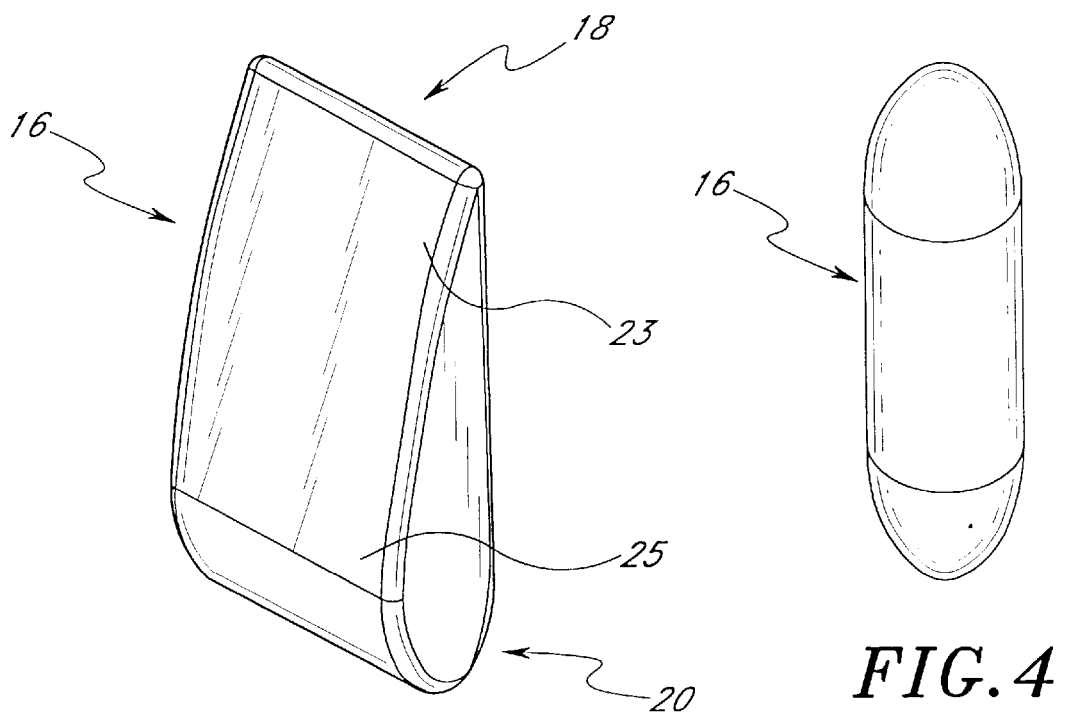
FIG. 3
FIG. 4
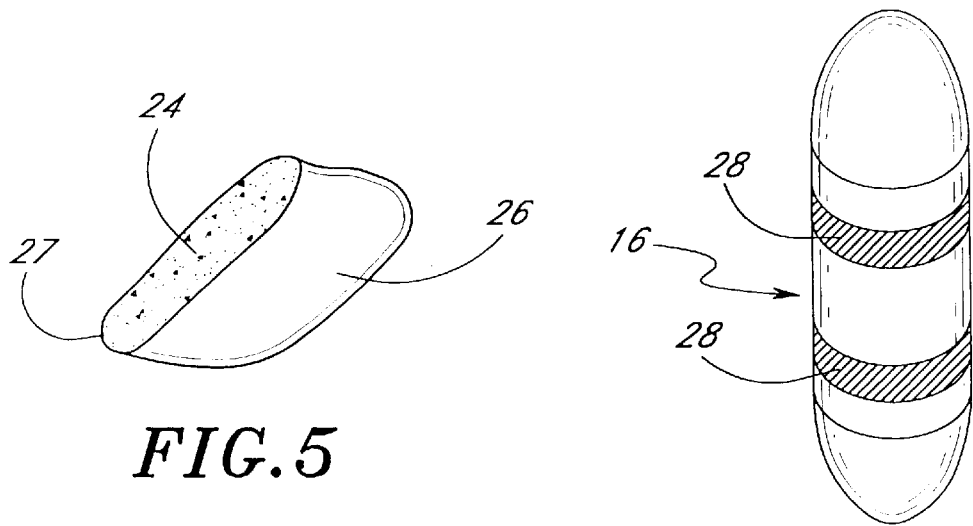
FIG. 5
FIG. 6

SUBMUCOSAL ESOPHAGEAL BULKING DEVICE

FIELD OF THE INVENTION

The present invention relates generally to the field of esophageal prosthetics. More specifically, a bulking prosthesis is disclosed for submucosal insertion to increase the closing pressure of the lower esophageal sphincter (LES).

BACKGROUND OF THE INVENTION

Gastroesophageal reflux is a physical condition in which stomach acids reflux, or flow back from the stomach into the esophagus. Frequent reflux episodes (two or more times per week), may result in a more severe problem known as gastroesophageal reflux disease (GERD). Gastroesophageal reflux disease is the most common form of dyspepsia, being present in approximately 40% of adults in the United States on an intermittent basis and some 10% on a daily basis.

Dyspepsia, or heartburn, is defined as a burning sensation or discomfort behind the breastbone or sternum and is the most common symptom of GERD. Other symptoms of GERD include dysphasia, odynophagia, hemorrhage, water brash, and pulmonary manifestations such as asthma, coughing or intermittent wheezing due to acid aspiration. Dyspepsia may also mimic the symptoms of a myocardial infarction or severe angina pectoris. Many factors are believed to contribute to the onset of GERD including transient lower esophageal sphincter relaxations, decreased LES resting tone, delayed stomach emptying, and an ineffective esophageal clearance. Many in the field agree, however, that the primary cause of GERD is the lack of competency of the lower esophageal sphincter.

The lower esophageal sphincter, or valve, is comprised of smooth muscle located at the gastroesophageal (GE) junction and functions to allow food and liquid to pass into the stomach but prevent regurgitation of stomach contents. At rest, the LES maintains a high-pressure zone between 10 and 30 mm Hg above intragastric pressure. Upon deglutition, the LES relaxes before the esophagus contracts, allowing food to pass through into the stomach. After food passes into the stomach, the LES contracts to prevent the stomach contents and acids from regurgitating into the esophagus. The mechanism of LES opening and closing is influenced by innervation via the vagus nerve and hormonal control of gastrin and possibly other gastrointestinal hormones.

The severity of GERD varies from patient to patient and in extreme cases complications including esophageal erosion, esophageal ulcers, and esophageal stricture are observed. Esophageal stricture is a serious condition which results from prolonged exposure of the esophageal mucosa to acid reflux. The most common clinical manifestation of stricture is dysphasia. Unlike dysphasia from non-strictured esophageal reflux, dysphasia caused by stricture is progressive in that the size of a bolus which can pass into the stomach progressively becomes smaller. In addition to esophageal erosion and ulceration, prolonged exposure of the esophageal mucosa to stomach acid can lead to a condition known as Barrett's Esophagus. Barrett's Esophagus is an esophageal disorder that is characterized by the replacement of normal squamous epithelium with abnormal columner epithelium. This change in tissue structure is clinically important not only as an indication of severe reflux, but the appearance of columner epithelium in the esophagus is indicative of cancer.

Current methods to treat gastroesophageal reflux disease consist of lifestyle changes such as weight loss, avoidance of certain foods that exacerbate the symptoms of GERD and avoidance of excessive bending. Elevation of the head of the bed helps prevent nocturnal reflux. While these avoidance strategies may be helpful, there is relatively little data supporting the efficacy of lifestyle modification alone for the treatment of GERD.

Medications for the treatment of GERD have been administered for years with little or no success. Conventional antacids, such as TUMS® and ROLAIDS®, produce short-term relief, but often have side effects including diarrhea and constipation. H2 receptor antagonists, such as Cimetidine and Ranitidine, are relatively more effective in controlling GERD symptoms but these symptomatic therapies fail to treat the underlying cause of the disease. More powerful secretory inhibitors, such as the proton pump inhibitors Omeprazole and Lansoprazole are more effective than the H2 antagonists but these drugs are expensive and, in the long term, produce negative side effects.

Surgery has become an attractive alternative for the treatment of GERD when lifestyle modification and medications fail to treat this debilitating condition. There are numerous reflux operations available which perhaps reflect the inadequacy of any one procedure to totally control the problem. The most commonly performed operation, Nissen Fundoplication, has been effective, but is often complicated by stricture formation or gas bloat syndrome. A laparoscopic Nissen procedure has also been developed, adding another dimension of difficulty, and long-term results remain questionable. In addition, a percutaneous laparoscopic technique has been developed. (See, for example, U.S. Pat. No. 5,006,106 to Angelchik). Minimally invasive techniques, such as transesophageal implantation of a prosthetic valve have also been attempted. (See, for example, U.S. Pat. No. 4,846,836 to Reich). Despite extensive attempts in the field to treat and prevent GERD, existing forms of treatment all have shortcomings.

In view of the foregoing, and notwithstanding the various efforts exemplified in the prior art, there remains a need for a minimally invasive bulking prosthesis and deployment methodology for transesophageal implantation into the vicinity of the lower esophageal sphincter.

SUMMARY OF THE INVENTION

There is provided in accordance with one aspect of the present invention, a method of treating gastroesophageal reflux disease. The method comprises the steps of identifying a patient having gastroesophageal reflux disease, and assessing the esophageal sphincter closing pressure. A submucosal esophageal bulking device is selected, for increasing the esophageal sphincter closing pressure. The device is inserted below the mucosa in the vicinity of the lower esophageal sphincter. The submucosally inserting step preferably comprises providing access through the mucosa and creating a space in the submucosa for receiving the esophageal bulking device.

In accordance with another aspect of the present invention, there is provided a method of treating gastroesophageal reflux disease. The method comprises the steps of providing an esophageal bulking device having a predetermined form, and inserting the gastroesophageal bulking device below the mucosa in the vicinity of the lower gastroesophageal sphincter. Preferably, the bulking device elevates the LES closing pressure to above about 15 mm Hg, more preferably to at least about 18 mm Hg, and optimally within the range of from about 20 mm to about 30 mm Hg.

Two or three or more gastroesophageal bulking devices may be implanted to achieve the desired closing pressure elevation. The method may further comprise the step of attaching the esophageal bulking device to adjacent submucosal or other tissue, such as by permitting cellular ingrowth into a porous surface on the esophageal bulking device. The method may further comprise the step of explanting the esophageal bulking device from the vicinity of the lower gastroesophageal sphincter. Preferably, the bulking device comprises a flexible, compressible preformed structure.

In accordance with another aspect of the present invention, there is provided an esophageal bulking device for implantation below the mucosa in the vicinity of the lower gastroesophageal sphincter. The bulking device comprises a flexible, compressible body, which comprises a compressible filler and an outer layer. The outer layer may be provided with a porous surface structure to permit cellular ingrowth. The bulking device has a preformed shape, having blunt, atraumatic edges. In one embodiment, the filler comprises an open celled foam, such as polyurethane.

Further features and advantages of the present invention will become apparent to those of skill in the art in view of the detailed description of preferred embodiments which follows, when considered together with the attached drawings and claims.

BRIEF DESCRIPTION OF THE DRAWINGS

FIG. 3 is a perspective schematic view of an esophageal bulking device of the present invention.

FIG. 4 is a perspective schematic view of another esophageal bulking device of the present invention.

FIG. 5 is a cross-sectional view of an esophageal bulking device of the present invention.

FIG. 6 illustrates an embodiment of an esophageal bulking device of the present invention having surface regions which promote tissue ingrowth.

DETAILED DESCRIPTION OF THE PREFERRED EMBODIMENT

Figure 1:
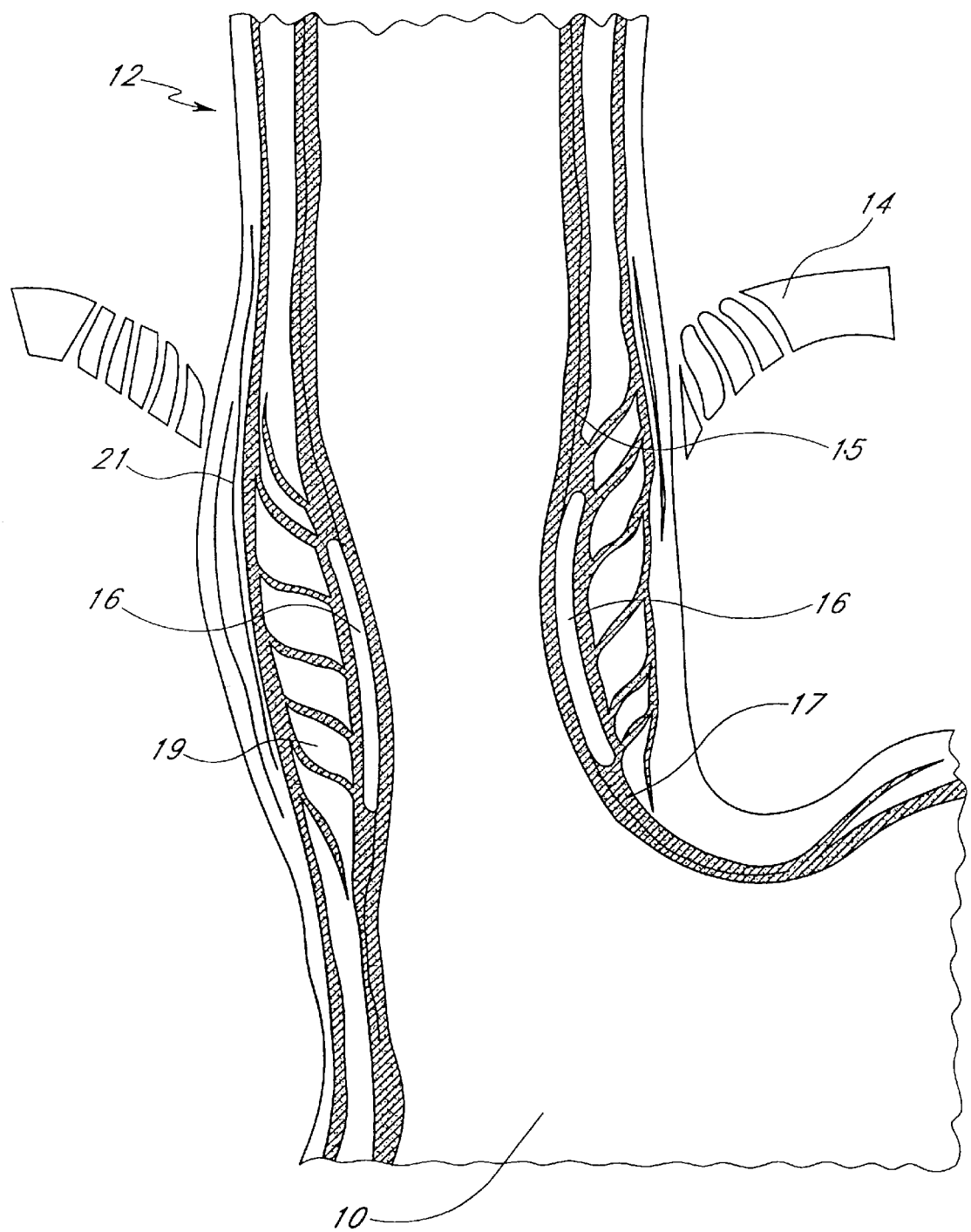
FIG. 1 is a schematic view of a pair of gastroesophageal bulking prostheses in accordance with the present invention, positioned at about the junction between the esophagus and the stomach, in which the LES is in an open configuration.

Referring to FIG. 1, there is illustrated a schematic representation of the stomach 10 and a portion of the lower esophagus 12. The esophagus 12 extends through the diaphragm 14, below which the esophagus 12 communicates with the interior of the stomach 10. A pair of gastroesophageal prosthetic bulking devices 16, in accordance with the present invention, is illustrated at about the junction between the lower esophagus 12 and the stomach 10.

In the illustrated embodiment, the bulking device 16 is implanted in the submucosa 17. The submucosa 17 is a fibrous layer of tissue positioned between the mucosa 15 and a layer of circular muscle 19. The circular muscle 19 is surrounded by a layer of longitudinal muscle 21, as is well understood in the art. The bulking device 16 is preferably implanted beneath the mucosa 15 as is discussed elsewhere herein. The bulking device 16 may either be implanted within the submucosa 17 as illustrated, or at the interface of adjacent tissue planes, such as between the mucosa 15 and submucosa 17, or between the submucosa 17 and circular muscle 19. Preferably, the bulking device 16 is implanted radially inwardly from the circular muscle layer 19.

Although the anatomy illustrated in FIG. 1 is generally normal, except for the improperly functioning native lower esophageal sphincter, the present invention is also useful in patients having lower esophageal abnormalities, such as hiatal hernia. In this condition, a portion of the wall of the stomach 10 extends upwardly through the diaphragm 14 and herniates superiorly to the diaphragm 14. The existence of a hiatal hernia or another abnormality in the lower esophagus may affect the implanted location of the esophageal prosthetic bulking device 16, but may not disqualify a patient otherwise treatable with the prosthetic bulking device 16 of the present invention.

As illustrated in FIG. 1, the esophageal bulking device 16 is generally implanted below the mucosa such as in the submucosa or between adjacent tissue planes in the vicinity of the sphincter. The submucosa is a springy tissue, which needs to be overexpanded in order to produce a cavity for implantation of the bulking device 16. Alternatively, the submucosa can be cut using mechanical cutting techniques or cautery tools as is discussed in more detail below.

Ideally, the esophageal bulking device 16 is implanted in a position that extends across or is closely adjacent the sphincter so that residual sphincter activity is optimized and the mucosal regions of the esophagus are protected from acid reflux. The precise positioning of the implant 16 depends largely on the patient's anatomy and the severity of GERD, and will be a matter of clinical choice at the time of implantation. In patients with a hiatal hernia, for example, the esophageal bulking device 16 is implanted as close as possible to the sphincter but care must be taken to insure that the hernia will not perturb the operation of the bulking device 16.

Figure 2:
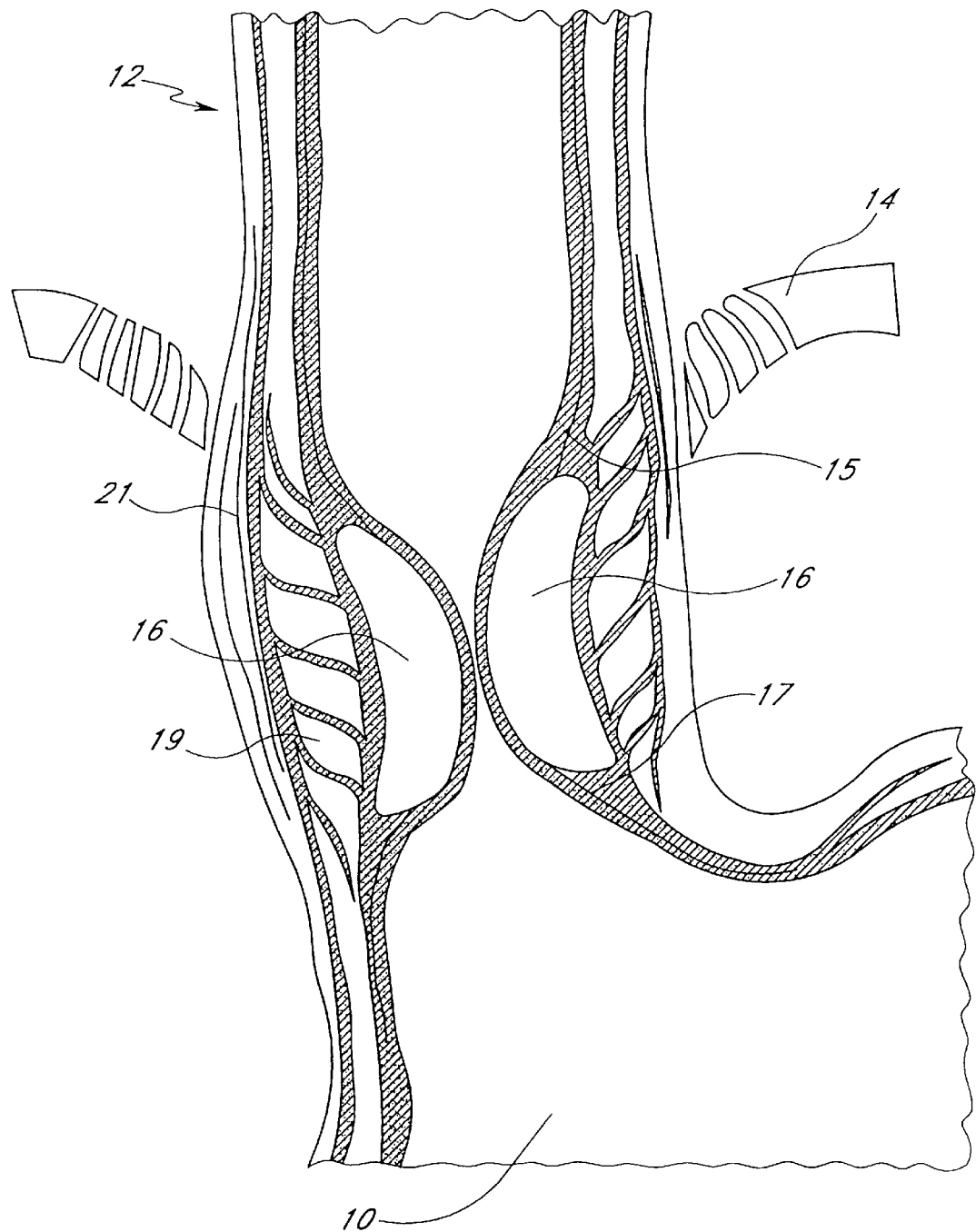
FIG. 2 is a schematic view of a pair of alternative gastroesophageal bulking prostheses in accordance with the present invention, positioned at about the junction between the esophagus and the stomach, in which the LES is illustrated in a closed configuration.

Advantageously, the esophageal bulking device 16 of the present invention enhances any residual closing pressure function of the sphincter so as to effectively reduce or prevent the reflux of stomach contents into the esophagus. In an open or relaxed state, as shown in FIG. 1, the esophageal bulking device allows food and liquid to pass through the esophagus into the stomach. However, when the sphincter is closed, as shown in FIG. 2, the esophageal bulking device increases the closing pressure along a sufficient axial length that, in cooperation with the contraction of the sphincter, it inhibits or prevents the reflux of stomach contents. In addition to illustrating the LES in the closed orientation, FIG. 2 illustrates a slightly modified bulking device 16 from that illustrated in FIG. 1.

Depending on the degree of LES dysfunction, more than one esophageal bulking device 16 can be implanted into the lining of the esophagus. Where two or three or more esophageal bulking devices 16 are utilized to improve LES function, the bulking devices 16 may be spaced around the circumference of the LES. Generally, multiple bulking devices 16 will be located substantially in the same transverse plane perpendicular to the longitudinal axis of the esophagus. Use of multiple bulking devices 16 without rigid interconnection permits the LES to radially expand to a greater degree so as to permit bolus passage and better accommodate the natural function of the esophagus.

Depending on the patient's anatomy and the extent of GERD, esophageal bulking devices 16 having various lengths and cross sectional profiles are implanted so as to maximize operation with the residual LES function. Using common esophageal manometry and endoscopic techniques, for example, medical personnel can measure the degree of closure (e.g., closing pressure) achieved by the sphincter as well as any unique anatomical features of the lower esophagus for a particular patient when selecting specific shapes and designs of esophageal bulking devices 16 to be implanted.

Due to the irregular cross-sectional configuration of the closed sphincter, the cross-sectional configuration of the bulking device 16 can take on any of a wide variety of shapes including, but not limited to, those specific embodiments disclosed herein. In general, the desired implanted transverse plane thickness of the esophageal bulking device 16 will depend on the lumen diameter and the extent of LES dysfunction. Devices 16 produced in accordance with the present invention can be rated according to their bulking area, which represents the total cross-sectional area the device will occupy within the region at or about to the sphincter, referred to as the "bulking zone". In general, a larger transverse cross-sectional area will produce a higher closing pressure for a given state of the disease.

FIGS. 3, 4, 5 and 6 illustrate different configurations and features of the esophageal bulking device 16 of the present invention. The esophageal bulking device 16 generally comprises an oblong, cylindrical, elliptical, toric or pillow shape and has a proximal end 18 and a distal end 20. As used herein, "distal" shall refer to a location closer to the stomach and "proximal" shall refer to a location closer to the mouth. In one embodiment, a proximal portion 23 has a smaller cross-sectional area than a distal portion 25. Alternatively, embodiments of the esophageal bulking device 16 can be a cylindrical shape (FIGS. 4 and 6) or elliptical shape (not illustrated) wherein a proximal portion 23 and a distal portion 25 have roughly the same cross-sectional area and shape. The bulking device 16 preferably substantially retains its pre-implanted configuration once implanted in the body.

Suitable esophageal bulking devices 16 comprise a soft, flexible body that may have an axial length from 1.0 cm to 5.0 cm, a width (circumferential implanted direction) of 0.2 cm to 2.0 cm, and a thickness (radial implanted direction) of 1.0 mm to 8.0 mm. Many esophageal bulking devices 16 of the present invention have a length within the range of 1.5 cm to 4.0 cm, a width within the range of 0.4 cm to 1.5 cm, and a thickness within the range of 1.5 mm to 6.0 mm. In one embodiment, the esophageal bulking device 16 has a length of 2.0 cm to 3.0 cm, a width of 0.8 cm to 1.0 cm, and a thickness of 4.0 mm to 6.0 mm.

Length to thickness ratios are generally no more than about 15:1 and are often no more than about 6:1 or 4:1. Length to thickness ratios on the order of less than 3:1 may also be desirable depending upon the severity of the condition. The cross-sectional area of the bulking device 16 may also vary at different points along the length of the same device 16. As mentioned above, optimal dimensions may be patient specific and can be determined through routine experimentation of one of skill in the art in view of the disclosure herein.

An LES having a relaxed open diameter of 2.0 cm, for example, has a cross-sectional lumen area of 3.14 cm$^2$. A 25% bulking function could be accomplished by providing a bulking device 16 having a total cross-sectional area in the bulking zone of about 0.785 cm$^2$. The bulking area may represent the area of an esophageal bulking device 16 having a generally oval or rectangular cross-section (e.g., 0.443 cm×1.772 cm) which is adapted to extend axially for a length of 1 to 3 cm beneath the mucosa.

In general, the objective of the present invention is to increase the closing pressure of the lower esophageal sphincter. The present inventors believe that a closing pressure of at least a certain minimum closing threshold value, maintained along a minimum axial effective LES length will satisfactorily reduce esophageal reflux. In the intra-abdominal (i.e., inferior to the diaphragm 14) esophagus, a minimum of about 2 cm of effective LES length appears desirable. An average pressure along that length is preferably in excess of about 15 mm Hg, preferably at least about 18 mm Hg, and optimally in the range of from about 20 mm to about 30 mm Hg.

Within certain outer limits, any increase in the closing pressure in the LES may improve symptoms. For example, some patients have an LES closing pressure on the order of about 5 mm Hg, which is accompanied by severe GERD symptoms. At the high end, a closing pressure in excess of about the minimum diastolic pressure inhibits blood flow, thereby increasing the risk of localized pressure necrosis. Pressure slightly below the minimal diastolic pressure may still interfere with swallowing function. The present invention therefore preferably enables increasing the closure pressure from a pretreatment value below about 14 or 16 mm Hg to a post treatment value of preferably on the order of from about 18 or 20 to about 25 or 30, along a length of at least about 1½ cm and preferably at least about 2 cm or 2.5 cm or more.

Once the total desired cross-sectional area and length of the bulking device is determined for a particular patient or class of patients, the allocation of that cross-sectional area to a single bulking device or a series of bulking devices which together produce the desired cross-sectional area must be determined. This clinical decision will take into account any unique aspects to the patient's lower esophageal anatomy, together with the extent of the disease and consequent total area of bulking required. In general, a larger single bulking device will require a larger submucosal pocket for implantation and the consequent greater disruption of tissue in the immediate area of the implant, which may be undesirable in some patients. In addition, a larger single device may have a greater likelihood of migration which would be reduced if the same total implant volume was implanted in two bulking devices each having half the cross-sectional area of the single larger device.

The bulking device 16 is preferably flexible and has a high degree of softness which approaches that of the native mucosal tissue, to minimize trauma to the adjacent tissue.

The material of the bulking device 16 is thus preferably soft enough so that is incapable of exerting sufficient localized pressure to cause pressure necrosis. A localized pressure in excess of about 70 mm Hg gives rise to a risk of localized tissue necrosis. As will be understood by those of skill in the art, the configuration of the bulking device 16 (e.g. sharp edges, etc.) operates in cooperation with the softness of the construction materials to optimize the compatibility of the bulking device. A smooth, blunt atraumatic outer surface is preferred.

One suitable bulking device construction comprises the use of an inflatable pillow or balloon, partially or completely filled with a liquid or semi-liquid, which allows one end to be compressed by peristaltic compression and the other end to expand bulbously. The ability of the volume of the bulking device to flow from one end of the bulking device to the other and back permits the passage of a peristaltic wave, as will be appreciated by those of skill in the art in view of the disclosure herein. Suitable elastomeric balloons comprise material such as silicone, latex and others as will be understood by those of skill in the art.

In addition to being soft, the bulking device in some embodiments may also be compressible. This enables the filler 24 and body of bulking device 16 to expand when nothing is passing through the LES, but compress, for example, to no more than about 4 mm and preferably no more than about 2 mm in radial thickness during swallowing. After swallowing, the filling material 24 and body will desirably rebound back to facilitate the LES closure function. In this manner, the bulking device 16 can cooperate with any residual function of the LES to minimize the occurrence of reflux.

Referring to FIG. 5, the bulking device 16 generally comprises an outer surface 26 which encloses a filler 24 therein. The outer surface 26 may be homogeneous with the filler 24, or may be the surface of a dissimilar material in the form of a flexible wall 27 to encapsulate the filler. A homogeneous material outer wall 27 may be provided with a different physical property than the filler 24, such as by heat treatment, solvent exposure or the like to provide a barrier coating around the filler 24.

The esophageal bulking device 16 can be manufactured as a unitary or multi-component structure in a variety of ways as will be appreciated by those of skill in the art in view of the disclosure herein. The bulking device 16, for example, may be a unitary structure molded as a single piece of biocompatible foam material such as silicone foam or polyurethane foam, or may be cut from a block of such foam. Such foam parts can be made with an outer skin 26 of porous foam that facilitates tissue ingrowth.

Alternatively, the esophageal bulking device 16 can comprise a body having at least two components connected together and can be made, for example, by positioning an outer sleeve or layer 27 of porous material such as expanded polytetraflouroethylene (PTFE) or other tissue ingrowth material around the filler 24 by either a simple filling operation or by bonding the two materials together. If expanded PTFE is used, a PTFE surface etching step prior to bonding with a silicone based glue may be performed. Alternatively, a process of gluing by simultaneously compressing and heating a stack-up of foam, glue and PTFE can be employed. The outer layer 27 may be secured to the bulking device 16 in any of a variety of manners, such as by solvent bonding, thermal bonding, adhesives, and others as will be apparent to those of skill in the art in view of the disclosure herein.

The present inventors further contemplate embodiments of the esophageal bulking device 16 which have surface textures, coatings or structures to resist migration. In general, the entire outer surface 26 of the outer layer 27 or filler 24 can be coated or textured to facilitate tissue attachment such as by cellular ingrowth. The resulting attachment surface 26 can be integral with the bulking device 16 or can be directly or indirectly connected to the bulking device 16 so that the device 16 can be positioned and retained in the desired position within the esophageal wall. The outer surface 26 may additionally, or alternatively, be provided with any of a variety of tissue retention structures such as hooks, barbs, tacks, clips, sutures, staples, tissue adhesives, attachment strips, attachment spots, attachment connectors, or other attachment means which will be understood by those of skill in the art in view of the disclosure herein.

As illustrated in FIG. 6, one embodiment of the present invention is alternatively provided with one or more attachment surfaces 28 spaced about the device 16 so as to facilitate tissue ingrowth from the adjacent tissue over less than the entire surface 26 of the implant. The design, spacing and total surface area of the attachment surfaces 28 can be varied widely, depending upon the clinical objective.

For example, in an embodiment in which removal is not anticipated, the tissue ingrowth surface area can be as high as 75% to 100% of the surface 26 of the bulking device 16. Alternatively, in an application where the bulking device 16 is preferably removable after a period of time, the percentage of cellular ingrowth surface is preferably kept to the minimum required to reasonably resist migration within the esophageal wall. Thus, in some embodiments, the tissue ingrowth surface 28 covers no more than about 20% and possibly no more than about 5% of the total surface area of the bulking device 16. In this manner, trauma to the tissue upon removal of the bulking device 16 can be minimized. The ease of removal of the bulking device 16 may be desirable because new implants which better accommodate the changing anatomy of the patient during the progression of the patient's LES disfunction and/or age may be indicated.

In one embodiment, one or more attachment zones 28 may extend circumferentially around the bulking device 16. Alternatively, the tissue ingrowth surfaces 28 may extend axially along the length of the esophageal bulking device 16. Further, the attachment zones 28 can be provided in the form of spots or patches distributed around the surface of the esophageal bulking device 16.

The porosity of the cellular ingrowth regions 28 may range from about 20 μm to about 100.0 μm or greater. Desirably, the porosity of the cellular ingrowth regions 28 ranges from 20 μm to 50 μm and, in many embodiments, the porosity of the cellular ingrowth regions 28 ranges from 20 μm to 30 μm.

Suitable outer layer 27 and/or attachment surface 28 materials include polytetrafluoroethylene (PTFE), polyethylene terephthalate, polyester, polyurethane, silicone, dacron, polypropylene knit, and other materials which will be apparent to those of skill in the art in view of the present disclosure. In one embodiment of the invention, the cellular ingrowth region 28 comprises PTFE having a 22 μm pore size. This porosity appears to permit shallow ingrowth into the esophageal bulking device 16 to prevent axial migration of the device 16 along tissue planes yet allows for relatively easy explant.

Implantation of the esophageal bulking device 16 below the mucosa can be accomplished in any of a variety of ways, as will be apparent to those of skill in the art in view of the disclosure herein. Delivery systems can be specially constructed or assembled from existing endoscopic and other surgical tools to accomplish the basic implantation steps.

In general, the implantation site for a particular patient is identified, such as by endoscopy and manometry. Tissue adjacent to the implantation site is preferably immobilized to permit a puncture or incision to be made. Immobilization of the esophageal lining may be accomplished by grasping the tissue utilizing forceps, such as those which may be advanced through a working channel on an endoscope. Alternatively, a vacuum may be applied to a lumen through an endoscope to grasp tissue.

Using counter-traction on the tissue applied by way of the tissue grasper, the mucosa is pierced to enable insertion of the prosthesis. The mucosal layer may be pierced in a variety of ways, as will be recognized in the art. In accordance with one aspect of the present method, a needle is utilized to pierce the mucosa and create a blister by injecting a volume of fluid such as saline solution. Alternatively, an electrocautery cutter or any of a variety of sharp dissection tools may be utilized to pierce the mucosa and provide access to the submucosal area.

Once an aperture has been formed in the mucosa, a pouch is formed in the submucosa. The pouch may be formed by liquid infusion to enlarge the blister discussed above. Alternatively, any of a variety of blunt tools may be utilized to achieve a blunt dissection in the submucosa or between adjacent tissue planes to form a pouch for receiving the prosthesis. Alternatively, an inflation device, such as a balloon, may be specially shaped for insertion and inflation to separate submucosal tissue and provide a submucosal pouch.

Following formation of a submucosal pouch, one or more bulking devices 16 are introduced therein. The bulking device 16 may be inserted by way of a grasper, clamshell deployment device, or other tools. Depending upon the shape and compliancy of the bulking device 16, the bulking device 16 may be deployed from the distal end of a tubular element, such as by advancing an axially moveable core to push the prosthesis from the distal end of the tube. One or more pull elements such as wires, strings or tabs may be provided on the bulking device 16, so that a distally extending pull element may be advanced into the pouch under distal force using a grasper, or a second mucosal puncture inferior to the primary mucosal puncture may be provided through which to pull a pull element, thereby advancing the bulking device 16 inferiorly into the pouch.

Following placement of the bulking device 16 into the submucosal pouch, the mucosal opening is preferably closed using any of a variety of closure techniques. A conventional suture, ligating bands or staples or other clips, may be utilized endoscopically, as will be understood in the art. Alternatively, a topical glue or other adhesive patch may be utilized to close the opening in the mucosa.

Figure 7:
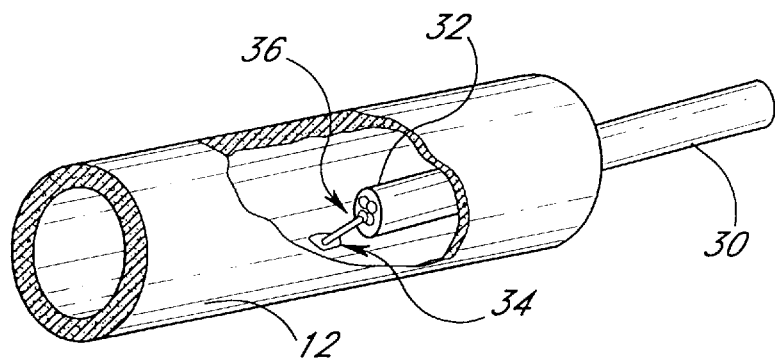
FIG. 7 is a fragmentary perspective view of an endoscope positioned within the esophagus prior to formation of a pocket for receiving a bulking device.
Figure 8:
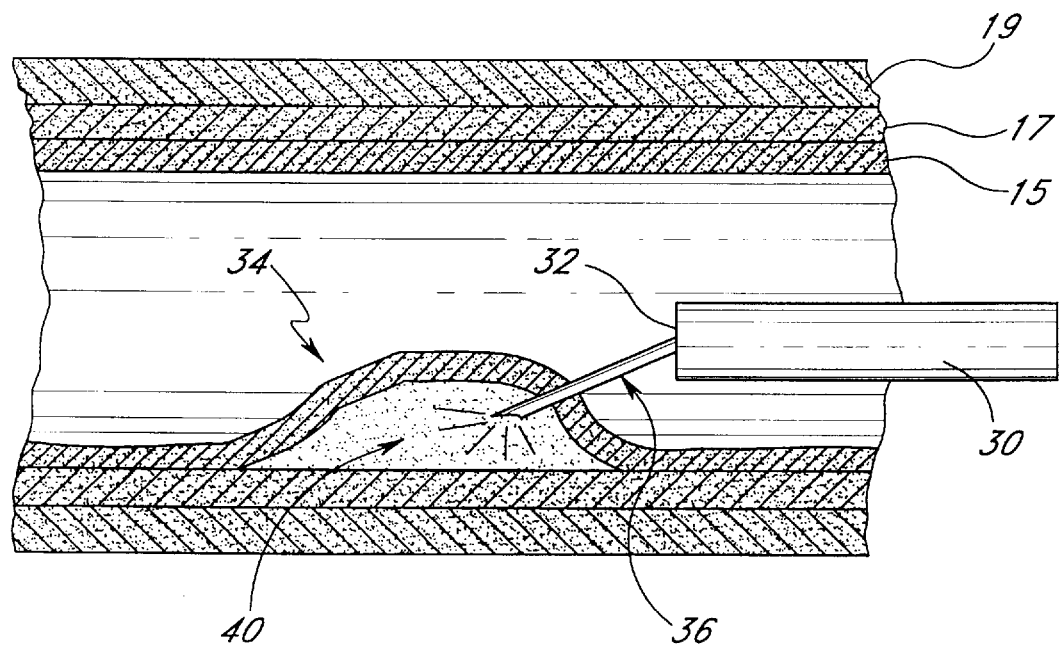
FIG. 8 is a schematic cross-sectional view of the endoscope positioned within the esophagus, forming a pocket by liquid injection.

Thus, referring to FIGS. 7 and 8, there is schematically illustrated one method of providing a blister or pocket below the mucosa. A portion of the esophagus 12 is illustrated, having a mucosa 15, submucosa 17 and circular muscle layer 19. An endoscope 30 is nasally or orally introduced and trans-esophageally advanced until a distal end 32 is positioned in the vicinity of the desired bulking device implantation site. A portion 34 of the mucosa 15 is raised into a blister, such as by introduction of a hypodermic needle 36 from the distal end 32 of endoscope 30. Hypodermic needle 36 is utilized to inject a fluid media 38 such as n-saline or other biologically acceptable material below the mucosa 15 to form a blister 40. Proper positioning of the hypodermic needle 36 can be ascertained by tactile feedback as is understood in the art. Alternatively, the portion 34 of mucosa 15 can be raised from the submucosa 17, such as by application of a vacuum to the wall of the esophagus.

Figure 9:
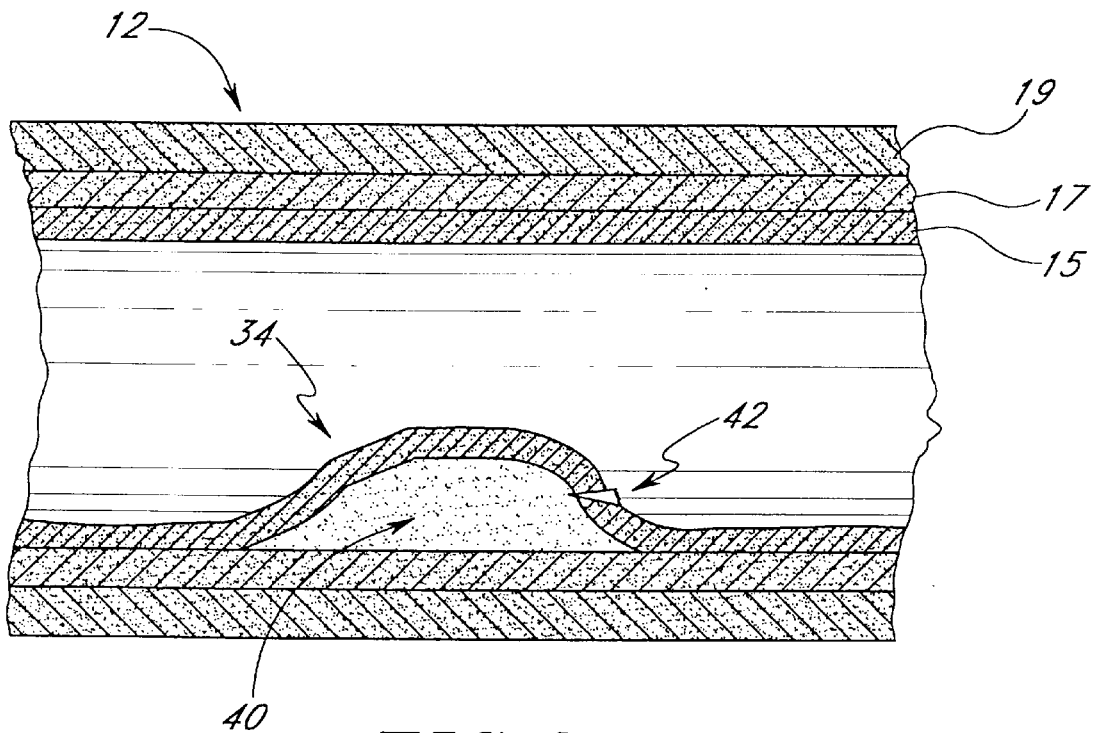
FIG. 9 is a side elevational view as in FIG. 8, illustrating an access incision.
Figure 10:
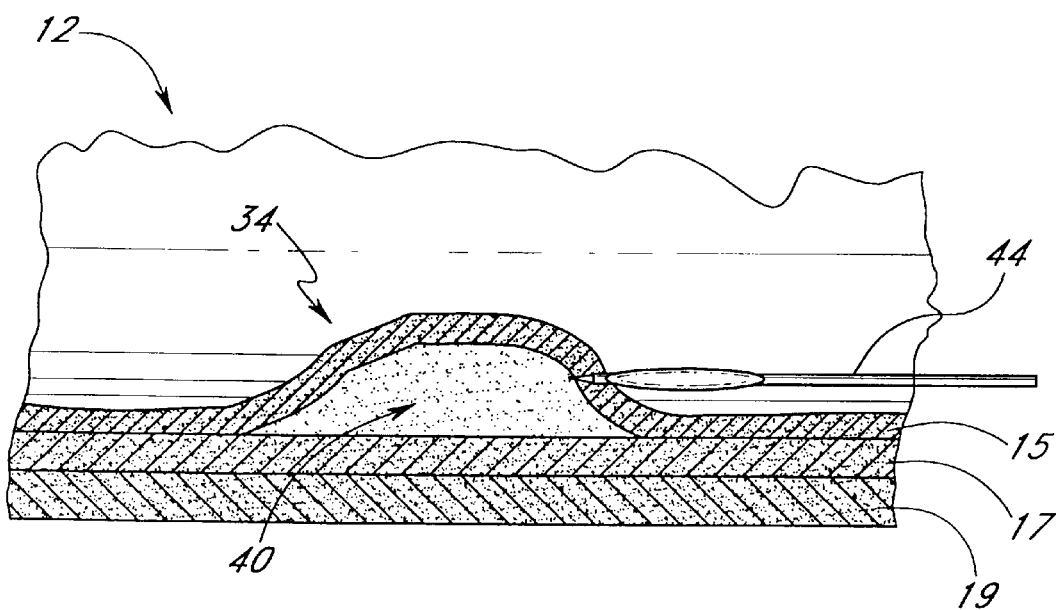
FIG. 10 is a side elevational view as in FIG. 9, illustrating a mechanical dilatation catheter during insertion into the blister.
Figure 11:
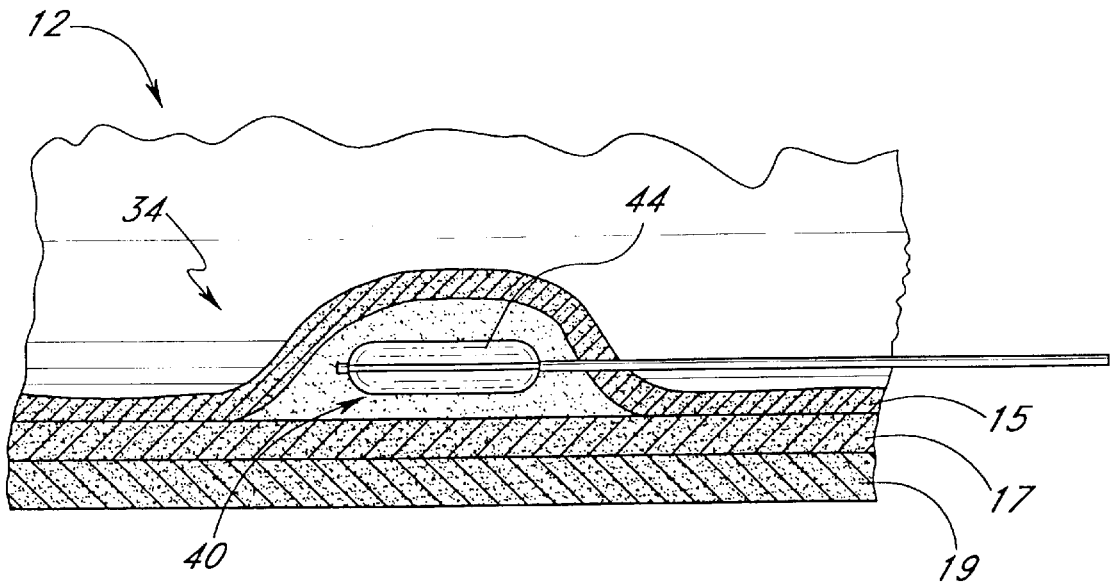
FIG. 11 is a side elevational view as in FIG. 10, with the mechanical dilatation catheter enlarged within the blister.
Figure 12:
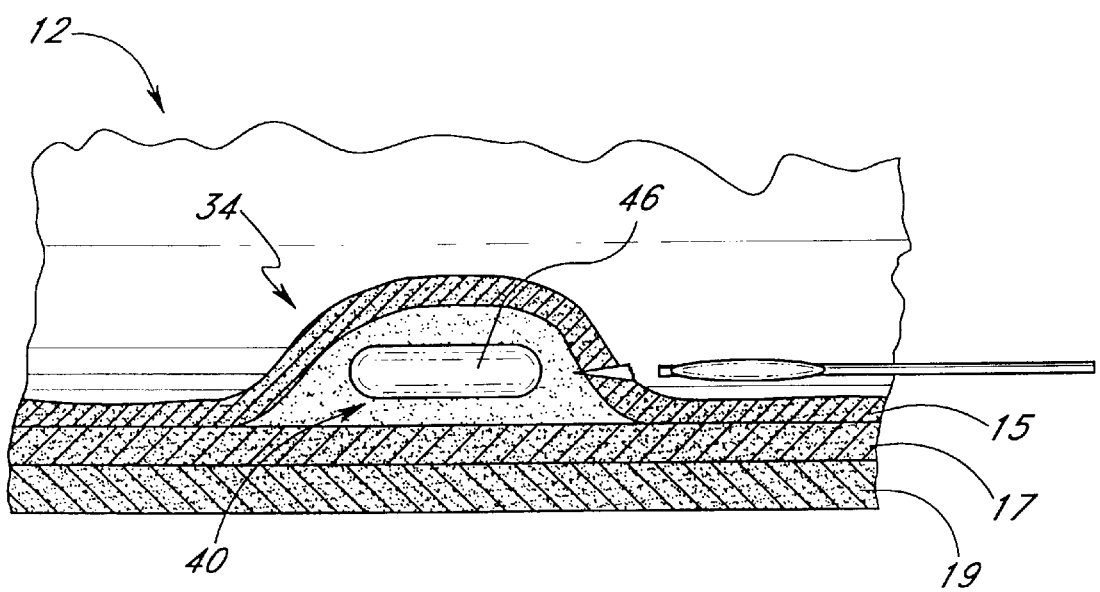
FIG. 12 is a side elevational view as in FIG. 11, illustrating the cavity formed by the dilatation catheter.

Following blister formation, a small incision or access site 42 is provided as illustrated in FIG. 9. A cavity formation device, such as a balloon dilatation catheter 44, is introduced through the access site 42 and into the blister. The balloon 46 is inflated, thereby forming a pocket 40 within the esophagus wall. If the bulking device 16 is to be implanted within the submucosa 17, the balloon dilatation catheter 44 must generally inflate to a larger volume than the volume of the bulking device 16, due to recoil of the fibrous tissue in the submucosa 17.

Following dilatation or manipulation of another pocket forming device, the balloon dilatation catheter 44 or other device is reduced in size and removed, thereby leaving a receiving cavity 46 for one or more bulking devices 16. The bulking device 16 may then be inserted within the cavity using any of a variety of delivery implements, the specific design of which will depend upon the size and configuration of the bulking device 16. The foregoing steps may be repeated for two or more positions around the circumference of the esophagus in the vicinity of the LES, as may be desired.

Figure 13:
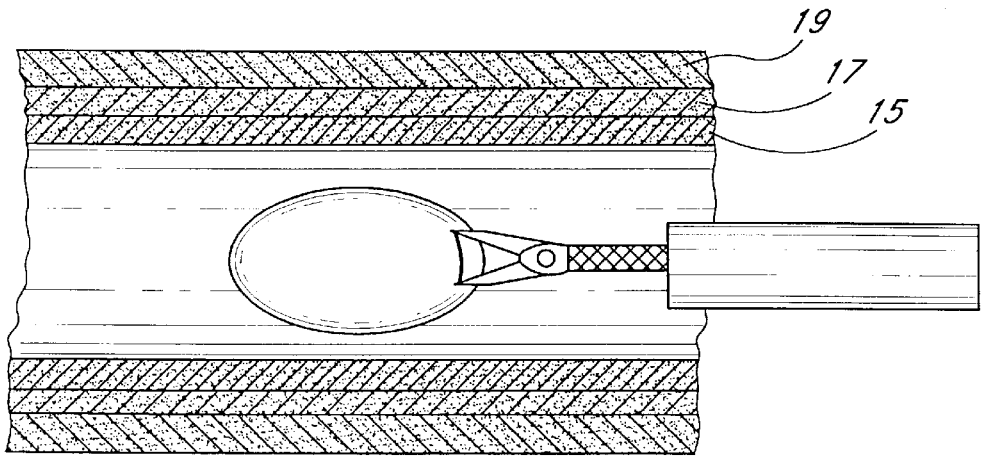
FIG. 13 is a top view of a blister, prior to forming a pocket with a cutting tool.
Figure 14:
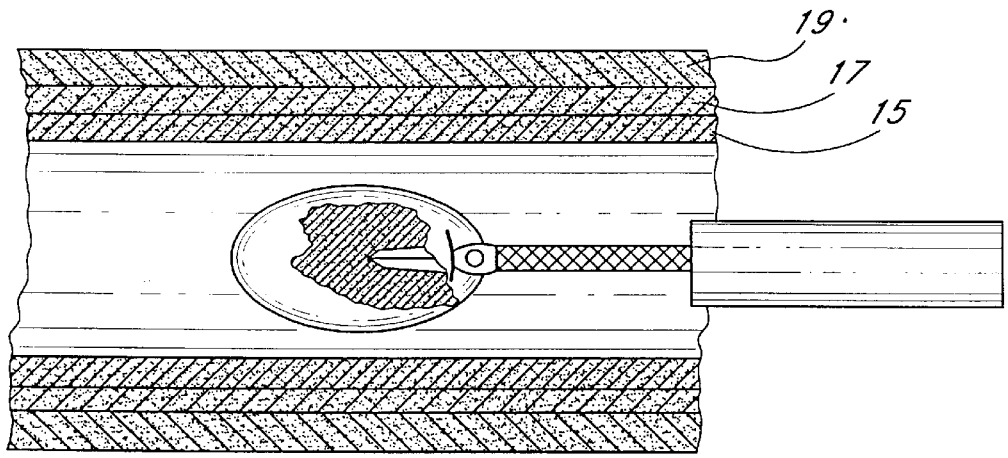
FIG. 14 is a top view as in FIG. 13, with the cutting tool inserted within the blister.
Figure 15:
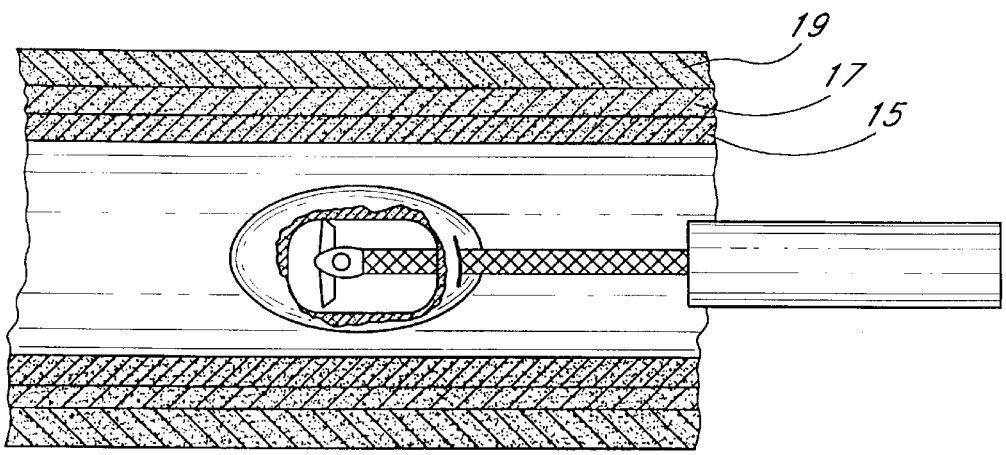
FIG. 15 is a top view of the blister as in FIG. 14, with the cutting tool cutting a pocket in the fibrous submucosa layer.

An alternate method of forming the cavity 46 is illustrated in FIGS. 13–15. In this embodiment, a mechanical cutting device, such as a scissor 48, is introduced below the mucosa 15 and manipulated to sever the springy tissue of the submucosa 12 and produce a cavity 46 for receiving the submucosal bulking device 16.

Any of a variety of different mechanical or electrical devices may be utilized as will be apparent to those of skill in the art in view of the disclosure herein, for producing the cavity 46 for receiving one or more bulking devices 16.

Although the foregoing invention has been disclosed in terms of certain preferred embodiments, other specific embodiments can be constructed in view of the disclosure herein without departing from the spirit of the scope of the present invention. Accordingly, the scope of the Applicant's invention is to be determined by reference to the attached claims, which are not limited to any of the particular embodiments disclosed herein.

What is claimed is:

1. A method of treating gastroesophageal reflux disease comprising providing an esophageal bulking device having a predetermined form and inserting the gastroesophageal bulking device below the mucosa in the vicinity of the lower esophageal sphincter.

2. The method of claim 1, wherein the inserting step comprises inserting two or more bulking devices.

3. The method of claim 1, wherein the bulking device comprises a flexible outer shell and a filling material.

4. The method of claim 1, further comprising the step of attaching the esophageal bulking device to adjacent tissue.

5. The method of claim 4, wherein the attaching step comprises permitting cellular ingrowth into a porous surface on the esophageal bulking device.

6. The method of claim 1, further comprising the step of explanting the esophageal bulking device from the vicinity of the lower esophageal sphincter.

7. A method of treating gastroesophageal reflux disease, comprising the steps of:

identifying a patient having gastroesophageal reflux disease;

assessing the esophageal sphincter closing pressure;

selecting a submucosal esophageal bulking device which corresponds to the esophageal sphincter closing pressure; and submucosally inserting the gastroesophageal bulking device in the vicinity of the lower esophageal sphincter.

8. A method as in claim 7, wherein the cross-sectional area of the gastroesophageal bulking device is selected to compensate for deficiency in the intraesophageal closing pressure achieved by the gastroesophageal sphincter.

9. An esophageal bulking device for implantation below the mucosa in the vicinity of the lower esophageal sphincter, comprising a flexible body.

10. An esophageal bulking device as in claim 9, wherein the flexible body further comprises a filler and an attachment surface which allows tissue ingrowth from adjacent tissue in the vicinity of the lower esophageal sphincter.

11. The esophageal bulking device of claim 9, wherein the flexible body has a preformed elongate structure with blunt, atraumatic edges.

12. The esophageal bulking device of claim 9, comprising an oblong shape having a proximal end and a distal end such that the proximal end has a smaller cross-section than the distal end.

13. The esophageal bulking device of claim 10, wherein the attachment surface comprises a porous surface.

14. The esophageal bulking device of claim 10, wherein the filler comprises a material selected from the group consisting of silicone, polyurethane, polysulfone, hydrogels, and polyester.

15. The esophageal bulking device of claim 10, wherein the filler comprises a biocompatible foam.

16. The esophageal bulking device of claim 10, wherein the attachment surface has a pore size within the range of from about 20 μm to 100 μm.

17. The esophageal bulking device of claim 10, wherein the attachment surface and flexible body comprise a unitary structure.

18. The esophageal bulking device of claim 10, wherein the attachment surface and flexible body comprise at least two components connected together.

19. The esophageal bulking device of claim 10, wherein the filler is a biocompatible liquid or gel selected from the group consisting of saline, silicone oil, DMSO, polyvinyl, pyrollidone and hydrogels.

20. A method of increasing the closing pressure in the lower esophageal sphincter, comprising the steps of:

trans-esophageally introducing an endoscope to a treatment site in the vicinity of the lower esophageal sphincter;

providing an access pathway through the mucosa; and introducing a bulking device into the wall of the esophagus below the mucosa, so that the bulking device cooperates with the lower esophageal sphincter to increase the closing pressure of the sphincter.

21. A method as in claim 20, wherein the bulking device increases the closing pressure of the sphincter along an axial length of at least about 1.5 cm.

22. A method as in claim 20, wherein the closing pressure following implantation of the bulking device is at least about 18 mm Hg.

23. A method as in claim 22, wherein the closing pressure in the lower esophageal sphincter is within the range of from about 20 mm Hg to about 30 mm Hg.

24. A method as in claim 21, wherein the closing pressure following implantation of the bulking device is at least about 18 mm Hg along a length of at least about 2 cm.

* * * * *